United States Patent
Hara et al.

(10) Patent No.: US 8,652,533 B2
(45) Date of Patent: Feb. 18, 2014

(54) DURABLE BIOCIDES AND DISINFECTANTS

(75) Inventors: Yukihiko Hara, Tokyo (JP); Paul Wegener, New York, NY (US)

(73) Assignee: Mitsui Norin Co., Ltd., Tokyo (JP)

( * ) Notice: Subject to any disclaimer, the term of this patent is extended or adjusted under 35 U.S.C. 154(b) by 1452 days.

(21) Appl. No.: 11/571,626

(22) PCT Filed: Jul. 5, 2005

(86) PCT No.: PCT/US2005/023351
§ 371 (c)(1),
(2), (4) Date: Aug. 15, 2007

(87) PCT Pub. No.: WO2006/083318
PCT Pub. Date: Aug. 10, 2006

(65) Prior Publication Data
US 2008/0096959 A1    Apr. 24, 2008

Related U.S. Application Data

(60) Provisional application No. 60/586,261, filed on Jul. 7, 2004.

(51) Int. Cl.
*A61K 36/00* (2006.01)
*A61K 36/82* (2006.01)

(52) U.S. Cl.
USPC ........................................... 424/725

(58) Field of Classification Search
None
See application file for complete search history.

(56) References Cited

U.S. PATENT DOCUMENTS

| | | |
|---|---|---|
| 5,747,053 A | 5/1998 | Nashimoto et al. |
| 5,888,527 A | 3/1999 | Nashimoto et al. |
| 7,332,475 B2 | 2/2008 | Furukawa et al. |
| 2002/0028281 A1* | 3/2002 | Omura .................... 426/597 |
| 2003/0086986 A1 | 5/2003 | Bruijn et al. |
| 2005/0148658 A1* | 7/2005 | Hensley .................. 514/456 |
| 2006/0147989 A1* | 7/2006 | Rosenbloom ............ 435/6 |

FOREIGN PATENT DOCUMENTS

| | | |
|---|---|---|
| EP | 1133999 | 9/2001 |
| JP | 1-265023 | 10/1989 |
| JP | 09-110615 | 4/1997 |
| JP | 2000-44473 | 2/2000 |
| JP | 2005314316 | 11/2005 |
| JP | 2006021095 | 1/2006 |
| WO | WO2004012655 A2 * | 2/2004 |
| WO | 2005007640 | 1/2005 |

OTHER PUBLICATIONS

Morisawa, Y., "Development of Medicals", 2003, vol. 205, No. 11, pp. 881-883.

* cited by examiner

*Primary Examiner* — Terry A McKelvey
*Assistant Examiner* — Randall Winston
(74) *Attorney, Agent, or Firm* — Fish & Associates, PC

(57) ABSTRACT

Contemplated compositions and methods include a catechin at a concentration effective to inactivate SARS at least by a factor of 2 log 10 units when the formulation is applied to a surface. Preferably, the catechins are provided as a complex mixture, and most preferably as a near-native catechin preparation from green tea.

15 Claims, No Drawings

DURABLE BIOCIDES AND DISINFECTANTS

This application claims the benefit of our U.S. provisional patent application with the Ser. No. 60/586,261, filed Jul. 7, 2004, and which is incorporated by reference herein.

FIELD OF THE INVENTION

The field of the invention is antiviral compositions and methods.

BACKGROUND OF THE INVENTION

Viral diseases are often spread either directly via droplet transmission from one human to another human, or indirectly via an animal host that will then transfer the virus in a variety of manners. While numerous virucidal compositions are known in the art, most of them suffer form one or more disadvantage. Most notably, many synthetic compounds tend to be very expensive and often require uptake into a cell to inactivate a virus or stop viral propagation. Furthermore, and especially where synthetic compounds are topically applied, known compounds tend to be chemically aggressive.

Alternatively, natural compounds isolated from one or more plants can be employed as antiviral agents. For example, various anthraquinones and anthraquinone derivatives such as hypericin were demonstrated to be effective against certain viruses, especially in the presence of mild detergents (see e.g., Antiviral Res. 1991 September 16(2):185-96). While such compositions showed significant effect to certain viruses (e.g., vesicular stomatitis virus, herpes simplex type 1 and 2), they were substantially ineffective against other viruses (e.g., human rhinovirus). In other known applications, solid phase articles were impregnated with various plant extracts (e.g., green tea catechins) as described in U.S. Pat. Nos. 5,747,053 and 5,888,527 to Yashimoto et al. Other items (e.g., gargling cup) coated with green tea catechins were described by Hara in GB2300578, and sanitary goods impregnated with organic green tea extracts are taught by Matsutaka in EP 1133999. Once more, while such plant extracts showed significant viral inhibition on various impregnated articles, use of such articles was limited to impregnations. Furthermore, antiviral effect of such formulations is often inconsistent and specificity unpredictable. In still farther known topical applications of plant extracts, including green tea extracts, antibacterial and/or antifungal effect was reported in U.S. Pat. App. No. 2003/0086986. However, these formulations were not reported to have antiviral activity.

Reliable and significant antiviral compositions are especially desirable where the target virus is a rapidly spreading virus. One such example is the SARS coronavirus (SARS-CoV), which is an enveloped RNA virus that infects humans. Infected humans typically present a characteristic febrile illness with respiratory symptoms and myalgia, and many patients recover within a few days. However, a significant proportion progress to develop an atypical pneumonia, cumulating in an acute respiratory disease known as Severe Acute Respiratory Syndrome (SARS) with a fatality rate estimated to be about 15%.

SARS emerged as a disease in Southern China in November 2002 but has quickly spread to over 30 countries worldwide. The epidemic has now subsided, but a total of almost 8500 cases with over 800 deaths have been recorded. SARS-CoV is transmitted mainly by exposure to respiratory secretions. SARSCoV is most probably derived from a virus that naturally infects a wild or domestic animal. Thus, eradication will be difficult and periodic "re-emergence" from the animal reservoir is possible. For detailed additional information on SARSCoV, reference is made to the "Kamps-Hoffmann SARS reference" (by Flying publisher). Moreover, adaptation of the SARSCoV to humans may result in different patterns, or a higher frequency, of disease and vigilance is therefore advised as there are currently no known safe, non-toxic, and effective virucidal formulations that can be applied to materials, animals, and human.

Thus, while numerous compositions and methods with antiviral activity are known in the art, all or almost all of them suffer from one or more disadvantages. Consequently, there is still a need to provide improved compositions and methods for antiviral compositions, and especially topical antiviral formulations effective against SARSCoV.

SUMMARY OF THE INVENTION

The present invention is directed to compositions and methods of inactivation of various viruses, and especially SARSCoV using plant derived materials as virucidal component. Most preferably, the plant derived material comprises one or more catechins, and particularly green tea preparations.

Therefore, in one aspect of the inventive subject matter, a method of reducing the number of infectious SARS viruses on a surface has a step of contacting the surface with a composition comprising a catechin preparation, wherein the catechin preparation is present at a concentration effective to reduce the number infectious SARS viruses at least by a factor of 2 $\log_{10}$ units, and more preferably at least by a factor of 3.5 $\log_{10}$ units.

Viewed from a different perspective, a method of reducing spread of SARS virus ex vivo may comprise a step of contacting a virus carrier with a composition that includes a near-native catechin preparation from green tea, wherein the catechin preparation is preferably present in the composition at a concentration to inactivate SARS at least by a factor of 2 $\log_{10}$ units, and more preferably at least by a factor of 3.5 $\log_{10}$ units. Treated surfaces particularly include those that are in contact with a non-human animal (e.g., cage or corral), and/or at least part of the animal's body surface (e.g., skin, feather, hair, etc.). In further preferred aspects, the catechin preparation is prepared from green tea, and most preferably a green tea extract, a green tea extract powder, and/or a green tea concentrate. Depending on the particular formulation, the preparation can be administered in various manners. However, it is generally preferred that the preparation is applied as a spray, as a liquid on a wipe, or as a powder.

Consequently, a kit is contemplated that includes a liquid or powder formulation having a catechin at a concentration effective to inactivate SARS at least by a factor of 2 $\log_{10}$ units (and more preferably at least by a factor of 3.5 $\log_{10}$ units) when applied to a surface. Contemplated kits will further include an instruction to apply the formulation to a surface to thereby reduce a number of infectious SARS viruses on the surface.

Various objects, features, aspects and advantages of the present invention will become more apparent from the following detailed description of preferred embodiments of the invention.

DETAILED DESCRIPTION

The inventors discovered that various catechins, and especially green tea catechins can be effectively used as agents that reduce infectivity of a SARS (severe acute respiratory syndrome) virus ex vivo. Remarkably, the inventors discovered that the catechins exhibit anti-viral effect on various viruses, and particularly the SARS virus where the virus is exposed to the catechin on a solid phase and/or in a liquid phase before entering a host organism.

Consequently, in one aspect of the inventive subject matter, the inventor contemplates a method of reducing a number of infectious SARS viruses on a surface. In such methods, it is generally preferred that the surface is contacted with a composition that includes a catechin preparation, wherein the catechin preparation is present at a concentration effective to reduce the number infectious SARS viruses at least by a factor of 2 $\log_{10}$ units, and more preferably at least by a factor of 3.5 $\log_{10}$ units.

With respect to contemplated surfaces, it should be appreciated that the inventive subject matter is not limited to one or another surface, and that all surfaces are deemed suitable so long as such surfaces are exposed to potential contact with the SARS virus or even contain the SARS virus. For example, and among other suitable surfaces, especially preferred surfaces include those that are in contact with a non-human animal, and most typically a pet or animal used as a source of food. Thus, all structures suitable to at least temporarily guide and/or retain an animal (e.g., cage, corral, leash, fences, etc.) are particularly contemplated. Still further, and especially where numerous animas are kept at a relatively high density (e.g., stable, market, slaughterhouse, etc.) it is contemplated that the catechin preparation may also be applied to the surface of an animal. For example, the catechin preparation may be sprayed onto the animal, or the animal may be at least partially immersed in a solution containing the catechin preparation.

Preferably, the catechin preparation comprises at least one of an esterified catechin and a galloyl-containing catechin, and even more preferably a mixture of such catechins (optionally also comprising free catechins). For example, suitable catechin preparations may comprise one or more of (−)-Catechin Gallate, (−)-Epicatechin Gallate, (−)-Epigallocatechin Gallate, (−)-Gallocatechin Gallate, free Theaflavin, and Theaflavindigallate. Thus, among other preferred catechin preparations, complex extracts (e.g., Polyphenon-70A, Polyphenon-E, Polyphenon-60, Polyphenon-70, from Mitsui Norin) are especially contemplated. Further suitable compounds include tannins, including gallic and tannic acid. In yet further preferred aspects, the catechin preparation may also include a green tea extract (typically solvent-extract or $CO_2$ extract), green tea extract powder (e.g., freeze-dried extract or spray-dried green tea), and/or green tea concentrate which will typically (but not necessarily) include a solvent, and most typically water. In further contemplated aspects of the inventive subject matter, the catechin or catechin mixture will include an optionally additional carbohydrate portion that promotes hygroscopic properties of a surface that is coated or otherwise comprises catechins. Therefore, direct antiviral action may also be due to a tackifying effect in which the catechin retains the virus on the treated surface.

Therefore, in most preferred aspects, the catechin preparation will be sprayed or dusted onto the surface that is in need of treatment. Depending on the particular formulation, it is generally preferred that the concentration of the catechin is sufficient to inactivate SARS at least by a factor of 2 $\log_{10}$ units, more preferably at least by a factor of 3.0 $\log_{10}$ units, and most preferably at least by a factor of 3.5 $\log_{10}$ units. Consequently, the catechins will be present in the formulations at a concentration of between about 0.01 µM (or lower, e.g., where the formulation is repeatedly applied to the surface) to about 1.0 mM (or higher, e.g., where the formulation is a concentrate). However, and more typically the catechin concentration will preferably be between about 0.1 µM to about 100 µM. With respect to preferred formulations, it is contemplated that the catechin preparation may include one or more solvents (e.g., water, organic solvents [e.g., ethanol, DMSO, etc], and all reasonable combinations thereof), which may be miscible or form emulsions, multiple phases, liposomes, etc. Further contemplated ingredients especially include anionic, cationic, and neutral detergents. Therefore, suitable preparations may be formulated as a powder, spray, soap, or shampoo, and may be directly applied to the surface and/or together with water.

Viewed from another perspective, the inventor also contemplates a method of reducing spread of SARS virus ex vivo, wherein a virus carrier is contacted with a composition comprising a near-native catechin preparation from green tea. Most preferably, the near-native catechin preparation is present at a concentration to inactivate SARS at least by a factor of 2 $\log_{10}$ units units, more preferably at least by a factor of 3.0 $\log_{10}$ units, and most preferably at least by a factor of 3.5 $\log_{10}$ units. The term "near-native catechin preparation from green tea" as used herein refers to a preparation in which brewed green tea and/or green tea leaves are minimally processed (i.e., at least partially dehydrated, and/or pressed or otherwise macerated, which may be followed by solvent extraction that enriches the preparation in catechins) to form the preparation. Particularly preferred near-native catechin preparations include green tea extracts, green tea extract powders, green tea concentrates, each of which may or may not include one or more solvents.

With respect surfaces that are treated in such methods using contemplated compositions, the same considerations as provided above apply. Thus, it is generally preferred that surface is a virus carrier, which may be an animal or a surface in contact with the animal (e.g., cage, rail, corral, etc.), and/or which may be a surface that was previously exposed to a human infected with the SARS virus (e.g., bedding surface, garment surface, medical device, etc.)

Thus, the inventor also contemplates a kit that includes a liquid (e.g., spray or aerosol) or powder formulation comprising a catechin at a concentration effective to inactivate SARS at least by a factor of 2 $\log_{10}$ units, more preferably at least by a factor of 3.0 $\log_{10}$ units, and most preferably at least by a factor of 3.5 $\log_{10}$ units when the formulation is applied to a surface. Typically, an instruction is associated with the formulation to apply the formulation to a surface to thereby reduce a number of infectious SARS viruses on the surface. Typically, the instruction is provided as a printed matter on the container that encloses the formulation, but may also be provided as an independent printed (e.g., flyer, newspaper ad, etc.) or displayed (e.g., TV or Internet ad) information.

It should be appreciated that contemplated compositions are thought to reduce infectivity of a virus, wherein the reduction in infectivity need not necessarily be due to the reduction of the virus count. For example, and without wishing to be bound to any theory of hypothesis, the inventors contemplate that catechins may interact with the virus (and especially the virus coat) to render the virus less infective. Among other contemplated mechanisms, reduction in infectivity may be due to conformational changes in the virus coat, steric interaction with a viral docking protein, unspecific coating of the virus with the catechin, etc. Such discovery is particularly significant in light of the numerous problems associated with SARS as exemplarily described in Health Devices 2003 June 32(6) 220-2, which is incorporated by reference herein.

Depending on the particular use, the catechin may be disposed on a surface and the catechin-virus interaction will therefore be on or near a solid phase. Such solid phase interaction is especially desirable in numerous application where a solid phase is contaminated with the virus. In fact, all fomites are contemplated herein. However, particularly contemplated solid phases will be (part of) materials that directly contact a viral source. For example, patient and/or care-giver garments, protective wear, or medical devices are deemed materials that directly contact a viral source. Alternatively, it is also contemplated that contemplated solid phases include materials that indirectly get exposed to the viral source. Such solid phases include those that receive the virus in an aerosolized form from a patient (e.g., via cough or sneeze) or other virus source (e.g., waste material, air-borne dust, etc.), liquid form (e.g., from biological fluid), or other manner of indirect transmission. Therefore, especially contemplated solid phases include garments, bedding, disposable covers, medical equipment, air filters and air ducts, respirators, masks, etc., and even walls, floors, ceilings, shades, and other components of a room or even building in which a patient and/or virus carrier was housed.

On the other hand, it is also contemplated that the catechin may be disposed in a solvent and the catechin-virus interaction will therefore be in a liquid phase. For example, especially suitable solvents include aqueous solvents, which may further include a stabilizer, bacteriostatic, and/or antiviral agent. For example, it is especially preferred that a catechin or catechin mixture is dissolved or dispersed in a solvent that is then aerosolized (or otherwise applied in liquid phase) to a surface that was, is, or will be exposed to a virus. Such liquid phase application is particularly desirable where a virus contaminated surface is to be disinfected, or where a locale is preemptively exposed to the catechins to reduce spread of the virus when the virus is introduced to the locale.

For example, it is contemplated that the catechin solution may be employed in a hand-wash, a spray, a detergent, or other wash- or rinse fluid for decontamination of a surface (e.g., the catechin solution may be added during the final cycle of a laundering process to coat the fabric, thus reducing the infectivity of any remaining virus and also coating the fabric with remaining catechin). On the other hand, catechins may also be used in a vaporizer, mister, humidifier, or other device (local or building-wide via air conditioner) to reduce infectivity of a virus in the air (e.g., may be introduced into a building as an aerosol and then circulated by moving air to coat the surfaces of the building including internal duct work and crevices not normally accessible to disinfection).

Still further, it should be recognized that contemplated compositions and methods need not be limited to treatment of a room or patient, but may also be especially useful in animal housing. For example, where the virus has an intermittent host (e.g., bird, pig, or other domestic animal), it is contemplated that the catechins may be used to reduce, if not even eradicate spread of the virus before the virus moves from the intermittent host to a human. Consequently, while reduction of infectivity of the SARS virus is particularly contemplated, other pathogens are also included. For example, contemplated pathogens include air-borne viruses, bacteria, and spores, as well as aerosols and other transmissible forms of such pathogens.

EXAMPLES

Cytoprotective Effect And Impact On Viability Of Various Catechins In Cells Infected With SARS (Toronto-2 Strain)

Cell viability was tested using the CellTiter-Glo Luminescent Cell Viability Assay from Promega. Similarly, % inhibition of viral infection (% CPE) at the indicated concentration was measured as known in the art and substantially as described below.

Vero 76 cells were plated at 10,000 cells/well in 50 µl DMEM (5% FBS, L-glutamate, medium must NOT contain phenol red) in barcoded plates. The cells were allowed to adhere overnight at 37° C. at 5% $CO_2$. 25 µl of the catechin solutions (see below) were added to the cells, and DMEM (5% FBS L-glut P/S (no phenol red)) was further added to the wells. Subsequently, 25 µl diluted virus (about 1:500 dilution of Toronto-2 virus in DMEM 5% FBS L-glut P/S) was added to wells. Cells with virus and catechins were incubated at 37° C. for 72 hours. Plates were then removed from incubator and allowed to come to room temperature for 30 minutes. 100 µl of GLO reagent was added to each well, and plates were shaken for 2 minutes on a plate shaker. The plates were then allowed to sit under the hood for 10 minutes. Signal acquisition was then performed using standard protocol in an Envision plate reader.

As can be clearly seen below, numerous tested catechins had cytoprotective effect against the SARS virus. Furthermore, almost all of the tested catechins failed to exhibit any apparent cytotoxicity when contacted with the catechins. Remarkably, only the esterified and/or galloyl-containing catechins [e.g., (−)-epicatechin gallate, (−)-epigallocatechin gallate, (−)-gallocatechin gallate], but not the free catechins [e.g., (+)-catechin, (+)-gallocatechin, (−)-epicatechin, (−)-epigallocatchin] had cytoprotective effect in the assay. The cytoprotective effect of catechins at the tested and relatively low concentration is particularly noteworthy since the data for that concentration failed to exhibit any indication that the catechin concentrations may be insufficient. Therefore, it is contemplated that antiviral concentrations may be significantly lower (e.g., between 0.1 and 1 µM, between 0.01 and 0.1 µM, or even lower) and still provide at least some antiviral effect.

In contrast, the IFN-beta (Interferon-beta) control incubations provided substantially no cytoprotective effect at a concentration of 50 International Units (IU), and showed at least some cytoprotective effect at a concentration of 50 IU. However, as IFN-beta also stimulated cell growth in the assay, the exact degree of cytoprotective effect is difficult to ascertain. The results for exemplary esterified or galloyl-containing catechins are listed in Table 1, while the results for free catechins are listed in Table 2. % CPE values of less than 30 were labeled inactive.

TABLE 1

| COMPOUND | TEST GROUP AND CONTROL (IFN-BETA) | % CPE (INHIBITION) | % CELL VIABILITY | CONC. (µM OR IU) | ACTIVITY |
|---|---|---|---|---|---|
| (−)-Catechin Gallate | CG | 100 | 100 | 1 | Active |
|  | IFN-beta | 378 | 313.95 | 500 | Active |
|  | IFN-beta | −2.61 | 265.99 | 50 | Inactive |

TABLE 1-continued

| COMPOUND | TEST GROUP AND CONTROL (IFN-BETA) | % CPE (INHIBITION) | % CELL VIABILITY | CONC. (µM OR IU) | ACTIVITY |
|---|---|---|---|---|---|
| (−)-Epicatechin Gallate | ECG | 100 | 100 | 1 | Active |
| | IFN-beta | 378 | 313.95 | 500 | Active |
| | IFN-beta | −2.61 | 265.99 | 50 | Inactive |
| (−)-Epigallocatechin Gallate | EGCG | 100 | 100 | 1 | Active |
| | IFN-beta | 378 | 313.95 | 500 | Active |
| | IFN-beta | −2.61 | 265.99 | 50 | Inactive |
| (−)-Gallocatechin Gallate | GCG | 100 | 100 | 1 | Active |
| | IFN-beta | 378 | 313.95 | 500 | Active |
| | IFN-beta | −2.61 | 265.99 | 50 | Inactive |
| free Theaflavin | TF | 53.27 | 100 | 1 | Active |
| | IFN-beta | 378 | 313.95 | 500 | Active |
| | IFN-beta | −2.61 | 265.99 | 50 | Inactive |
| Polyphenon-70A | P70A | 100 | 100 | 1 | Active |
| | IFN-beta | 378 | 313.95 | 500 | Active |
| | IFN-beta | −2.61 | 265.99 | 50 | Inactive |
| Polyphenon-E | PE | 100 | 100 | 1 | Active |
| | IFN-beta | 378 | 313.95 | 500 | Active |
| | IFN-beta | −2.61 | 265.99 | 50 | Inactive |
| Theaflavindigallate | TFDG | 100 | 100 | 1 | Active |
| | IFN-beta | 378 | 313.95 | 500 | Active |
| | IFN-beta | −2.61 | 265.99 | 50 | Inactive |

TABLE 2

| COMPOUND | TEST COMPD. AND CONTROL (IFN-BETA) | % CPE (INHIBITION) | % CELL VIABILITY | CONC. (µM OR IU) | ACTIVITY |
|---|---|---|---|---|---|
| (−)-Catechin | (−)C | 0 | 100 | 1 | Inactive |
| | IFN-beta | 378 | 313.95 | 500 | Active |
| | IFN-beta | −2.61 | 265.99 | 50 | Inactive |
| (+)-Catechin | (+)C | 8.17 | 100 | 1 | Inactive |
| | IFN-beta | 378 | 313.95 | 500 | Active |
| | IFN-beta | −2.61 | 265.99 | 50 | Inactive |
| (−)-Epigallocatechin | EGC | 25.82 | 100 | 1 | Inactive |
| | IFN-beta | 378 | 313.95 | 500 | Active |
| | IFN-beta | −2.61 | 265.99 | 50 | Inactive |
| (−)-Epicatechin | −EC | 6.21 | 70.07 | 1 | Inactive |
| | IFN-beta | 378 | 313.95 | 500 | Active |
| | IFN-beta | −2.61 | 265.99 | 50 | Inactive |
| (+)-Epicatechin | +EC | 12.09 | 100 | 1 | Inactive |
| | IFN-beta | 378 | 313.95 | 500 | Active |
| | IFN-beta | −2.61 | 265.99 | 50 | Inactive |
| (−)-Gallocatechin | −GC | 0 | 100 | 1 | Inactive |
| | IFN-beta | 378 | 313.95 | 500 | Active |
| | IFN-beta | −2.61 | 265.99 | 50 | Inactive |
| (+)-Gallocatechin | +GC | 6.21 | 37.41 | 1 | Inactive |
| | IFN-beta | 378 | 313.95 | 500 | Active |
| | IFN-beta | −2.61 | 265.99 | 50 | Inactive |
| Theaflavindigallate-A | TFDG-A | 15.03 | 100 | 1 | Inactive |
| | IFN-beta | 378 | 313.95 | 500 | Active |
| | IFN-beta | −2.61 | 265.99 | 50 | Inactive |
| Theaflavindigallate-B | TFDG-B | 6.21 | 100 | 1 | Inactive |
| | IFN-beta | 378 | 313.95 | 500 | Active |
| | IFN-beta | −2.61 | 265.99 | 50 | Inactive |

Inactivating Effect Of Various Complex Compositions Against SARS (Strain Urbani)

To distinguish an indirect antiviral effect that is at least in part due to the host cell from a direct virucidal effect (i.e., inactivation of the virus in a host-cell independent manner), the SARS virus was pre-incubated with various catechin-containing preparations. The so pre-treated virus was then added to cells substantially as described below.

SARSCoV, strain Urbani, was obtained from the Centers for Disease Control (CDC, Atlanta Ga.) and was grown in Vero 76 cells (American Type Culture Collection, Manassas, Va.). Cells were passaged in MEM containing 5% fetal bovine serum (Hyclone Laboratories, Logan, Utah). When doing virus titrations, gentamicin was added to 50 µg/ml, and serum was reduced to 2%. A variety catechin-containing preparations was obtained from Dr. Yukihiko Hara of Mitsui Norm Co., Ltd. of Tokyo, Japan, and added to the cell-virus mixture as follows.

To 180 µl of catechin-containing preparations (solubilized in the appropriate solvent or as already-prepared liquid) was added 20 µl of virus lysate having a titer of $10^{4-5}$ CCID/ml and the mixture was incubated at room temperature (−25° C.) for 60 min. To stop the incubation at a given time, a sample of the treated lysate was immediately diluted 1:10 in MEM containing 2% serum and titrated onto the Vero 76 cells. Surviving virus was assayed in triplicate by cytopathic effect (CPE) assay in Vero 76 cells using a tenfold dilution series. The virus was also incubated without test substance in compound solvent or MEM, under the conditions described above and assayed in parallel by CPE assay. The latter treatments served as virus controls. Results were expressed in Table 3 as $\log_{10}$ units relative to the controls (*sign denotes the catechin-containing preparation reduced the virus titer to below detectable limits).

TABLE 3

| ID | COMPOUND | $LOG_{10}$ REDUCTION IN VIRUS TITER |
|---|---|---|
| 1 | Canned Leaf Extract | 3.75 |
| 2 | Powdered Green Tea Extract | >3.75* |
| 3 | Green Tea Candy | 1.25 |
| 4 | Powdered Mix Stick | 1.0 |
| 5 | Catechin au lait | 2.0 |
| 6 | Concentrated Green Tea Liquid | 2.75 |
| 7 | Green Tea Extract Powder | >3.75* |
| 8 | Powder Green Tea Stick | 2.0 |
| 9 | Powder Black Tea Stick | 1.0 |
| 10 | Ready to Drink Green Tea | .75 |
| 11 | Concentrated Ready to Drink Green Tea | 1.0 |
| 12 | Pet Food with Green Tea | 3.75 |
| 13 | Throat Spray with Green Tea | 0.0 |
| 14 | Catechin Soap | >3.75* |
| 15 | 17 | >3.75* |
| 16 | Saline | 0.0 |

Table 4 lists the individual catechin content for selected catechins of the compounds of Table 3. All numbers are expressed as mg catechins per 100 mg or 100 ml as appropriate of the tested compound.

TABLE 4

| ID | GallicAcid | EGC | GC | EC | C | EGCg | GCg | ECg | Cg | Total |
|---|---|---|---|---|---|---|---|---|---|---|
| 1 | 0.000 | 0.007 | 0.002 | 0.002 | 0.001 | 0.007 | 0.000 | 0.001 | 0.000 | 0.019 |
| 2 | 0.000 | 0.790 | 0.132 | 0.197 | 0.042 | 1.194 | 0.026 | 0.235 | 0.000 | 2.616 |
| 3 | 0.001 | 0.050 | 0.014 | 0.014 | 0.004 | 0.073 | 0.014 | 0.015 | 0.002 | 0.186 |
| 4 | 0.000 | 0.000 | 0.000 | 0.000 | 0.000 | 0.006 | 0.000 | 0.000 | 0.000 | 0.006 |
| 5 | 0.000 | 0.191 | 0.021 | 0.062 | 0.011 | 0.403 | 0.000 | 0.081 | 0.000 | 0.769 |
| 6 | 0.578 | 0.510 | 0.661 | 0.123 | 0.141 | 0.009 | 0.003 | 0.002 | 0.005 | 1.454 |
| 7 | 0.000 | 4.000 | 0.400 | 1.000 | 0.200 | 6.100 | 0.200 | 1.200 | 0.100 | 13.30 |
| 8 | 0.000 | 0.890 | 0.092 | 0.224 | 0.039 | 1.181 | 0.047 | 0.206 | 0.032 | 2.710 |
| 9 | 0.115 | 0.062 | 0.028 | 0.081 | 0.055 | 0.317 | 0.000 | 0.264 | 0.013 | 0.820 |
| 10 | 0.800 | 5.200 | 10.00 | 1.200 | 3.000 | 7.700 | 8.700 | 1.500 | 1.900 | 39.10 |
| 11 | 1.800 | 22.90 | 32.70 | 8.100 | 8.70 | 36.10 | 34.00 | 10.20 | 6.800 | 159.6 |
| 12 | 0.000 | 0.029 | 0.007 | 0.012 | 0.006 | 0.030 | 0.000 | 0.007 | 0.009 | 0.100 |
| 13 | 2.000 | 31.50 | 11.80 | 15.70 | 4.90 | 67.10 | 5.000 | 20.00 | 1.400 | 157.5 |
| 14 | N/A | N/A | N/A | N/A | N/A | N/A | N/A | N/A | N/A | N/A |
| 15 | 0.000 | 2.600 | 0.300 | 0.700 | 0.100 | 3.600 | 0.100 | 0.700 | 0.100 | 8.100 |
| 16 | —/— | —/— | —/— | —/— | —/— | —/— | —/— | —/— | —/— | —/— |

As the above results clearly indicate, most of the catechin-containing preparations had a significant direct virucidal effect. Moreover, the most potent virucidal agents were near-native catechin preparation from green tea such as canned tea leaf extract, powdered green tea, green tea extract powder, pet foods with high concentrations of green tea extract, and catechin soap. Thus, and only with few exceptions, it appeared that the more processed the catechin-containing material was, the less direct virucidal activity was demonstrated. Remarkably, black tea products were not significantly virucidal as compared to the green tea products. One of the putative active components in green teas, catechin, was very also very inhibitory to the virus, especially in combination with a detergent.

Thus, specific embodiments and applications of durable biocides and disinfectants have been disclosed. It should be apparent, however, to those skilled in the art that many more modifications besides those already described are possible without departing from the inventive concepts herein. The inventive subject matter, therefore, is not to be restricted except in the spirit of the present disclosure. Moreover, in interpreting the specification, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of reducing a number of infectious SARS viruses on a fomite surface comprising:
    contacting the fomite surface with a composition that comprises a catechin preparation, wherein a plurality of infectious SARS viruses is present on the surface;
    wherein the catechin preparation comprises at least one of (−)-Catechin Gallate, (−)-Epicatechin Gallate, (−)-Epigallocatechin Gallate, and (−)-Gallocatechin Gallate;
    wherein the catechin preparation is present in the composition at a concentration effective to reduce via direct virucidal effect the number infectious SARS viruses at least by a factor of 2 $\log_{in}$ units when the composition is applied to the plurality of infectious SARS viruses on the fomite surface.

2. The method of claim 1 wherein the fomite surface is a surface of a structure in contact with a non-human animal.

3. The method of claim 1 wherein the catechin preparation has a concentration of between 0.1 μM to about 100 μM in the composition.

4. The method of claim 1 wherein the fomite surface is a selected from the group consisting of a garment, a bedding, a protective device, a medical device, a cage, a rail, a fence, and a corral.

5. The method of claim 1 wherein the catechin preparation predominantly comprises at least one of an esterified catechin and a galloyl catechin.

6. The method of claim 1 wherein the catechin preparation comprises an ingredient selected from the group consisting of a green tea extract, a green tea extract powder, and a green tea concentrate.

7. The method of claim 1 wherein the step of contacting the surface comprises spraying the catechin preparation onto the surface.

8. The method of claim 1 wherein the catechin preparation is present at a concentration effective to reduce the number infectious SARS viruses at least by a factor of 3.5 $\log_{10}$ units.

9. A method of reducing spread of SARS virus ex vivo comprising:
   contacting ex vivo a virus carrier that comprises a plurality of infectious SARS viruses with a composition comprising a near-native catechin preparation from green tea,
   wherein the composition comprises one or more of (−)-Catechin Gallate, (−)-Epicatechin Gallate, (−)-Epigallocatechin Gallate, (−)-Gallocatechin Gallate, free Theaflavin, and Theaflavindigallate;
   wherein the catechin preparation is present at a concentration to inactivate SARS at least by a factor of 2 $\log_{10}$ units via direct virucidal effect when the composition is applied to the plurality of infectious SARS viruses on the carrier; and
   wherein the (−)-Catechin Gallate, (−)-Epicatechin Gallate, (−)-Epigallocatechin Gallate, (−)-Gallocatechin Gallate, free Theaflavin, and Theaflavindigallate are present in the composition at a concentration of between 0.1 µM to 100 µM.

10. The method of claim 9 wherein the near-native catechin preparation is selected from the group consisting of a green tea extract, a green tea extract powder, and a green tea concentrate.

11. The method of claim 10 wherein the catechin preparation is present at a concentration to inactivate SARS at least by a factor of 3.5 $\log_{10}$ units.

12. The method of claim 9 wherein the virus carrier is an animal and wherein the step of contacting the carrier comprises spraying the catechin preparation onto the animal.

13. The method of claim 9 wherein the virus carrier is a surface in contact with an animal.

14. The method of claim 9 wherein the virus carrier is a surface that was previously exposed to a human infected with the SARS virus.

15. The method of claim 14 wherein the virus carrier is selected from the group consisting of a bedding surface, a garment surface, and a medical device surface.

* * * * *